United States Patent [19]

Becker

[11] Patent Number: 4,789,743

[45] Date of Patent: Dec. 6, 1988

[54] PROCESS FOR THE PREPARATION OF 2,4-DIAMINO-5-BENZYLPYRIMIDINES

[75] Inventor: Abram Becker, Raanana, Israel

[73] Assignee: Societe Anonyme: Sanofi Pharma S.A. - Succursale de Carouge, Geneve, Switzerland

[21] Appl. No.: 80,083

[22] Filed: Jul. 31, 1987

[30] Foreign Application Priority Data

Aug. 8, 1986 [FR] France ................. 86 11533

[51] Int. Cl.$^4$ ........................... C07D 239/28
[52] U.S. Cl. ................. 544/325; 544/349; 558/410; 558/408; 558/388; 549/434; 549/437; 549/439; 549/442; 549/445
[58] Field of Search ........................ 544/325

[56] References Cited

U.S. PATENT DOCUMENTS 3,671,564  6/1972  Cresswell et al. ............ 558/401
3,743,669  7/1973  Hillman et al. ............... 558/371

Primary Examiner—Mary C. Lee
Assistant Examiner—J. Richter
Attorney, Agent, or Firm—Foley & Lardner, Schwartz, Jeffery, Schwaab, Mack, Blumenthal & Evans

[57] ABSTRACT

The invention relates to a process for the preparaton of compounds of the formula I by reacting an alkali metal alcoholate with a compound of the formula II in the presence of an aliphatic ester such as methyl formate, and then condensing guanidine with the resulting compound of the formula III.

The compound of the formula II can be prepared by reacting the corresponding benzaldehyde with acrylonitrile in the presence of diazabicyclo-2,2,2,-octane.

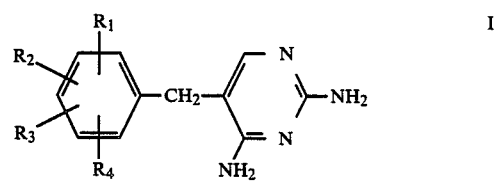

I

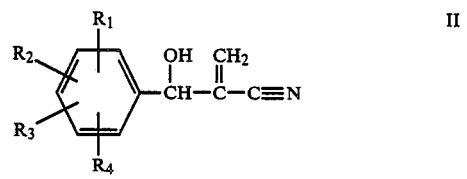

II

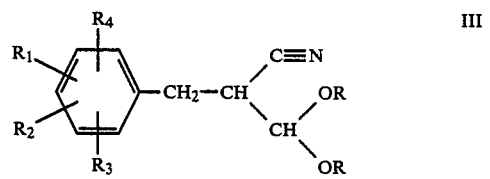

III

18 Claims, No Drawings

PROCESS FOR THE PREPARATION OF 2,4-DIAMINO-5-BENZYLPYRIMIDINES

The present invention relates to a novel process for the preparation of 2,4-diamino-5-benzylpyrimidines of the formula I:

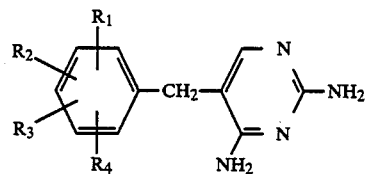
I in which $R_1$, $R_2$, $R_3$ and $R_4$, which are identical or different, represent hydrogen, a $C_1$ to $C_4$ alkyl group, a $C_1$ to $C_4$ alkoxy group, a halogen atom or a dialkylamino group in which the alkyl group is $C_1$–$C_3$, or $R_1$ and $R_2$ together represent a methylenedioxy group.

These compounds are antibacterial agents, especially the one in which $R_1$, $R_2$ and $R_3$, located in the 3, 4 and 5 positions of the phenyl nucleus, represent $OCH_3$, this compound being designated by the international common name: trimethoprim.

Numerous processes for the preparation of 2,4-diamino-5-benzylpyrimidines have been described. They correspond, for example, to the following reaction schemes, in which Z represents the various substituents of the phenyl nucleus:

SCHEME 1

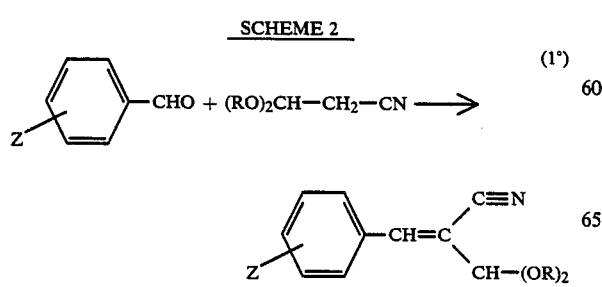

described in:
French Pat. No. 1266428 for R=alkyl
French Patent Document No. A-2361372 for R=O—(CH$_2$)$_n$—O—(CH$_2$)$_m$—CH$_3$, or

SCHEME 2

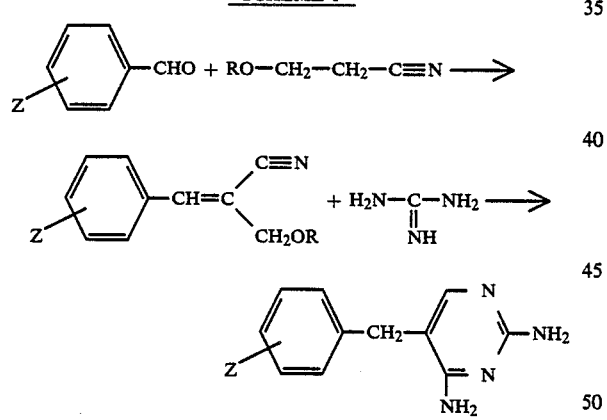

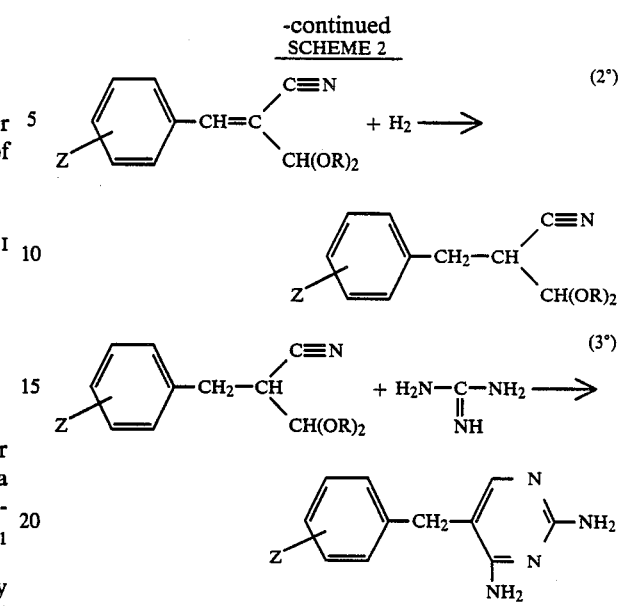

described in U.S. Pat. No. 3,671,564 and French Pat. No. 1 497 933, or

SCHEME 3

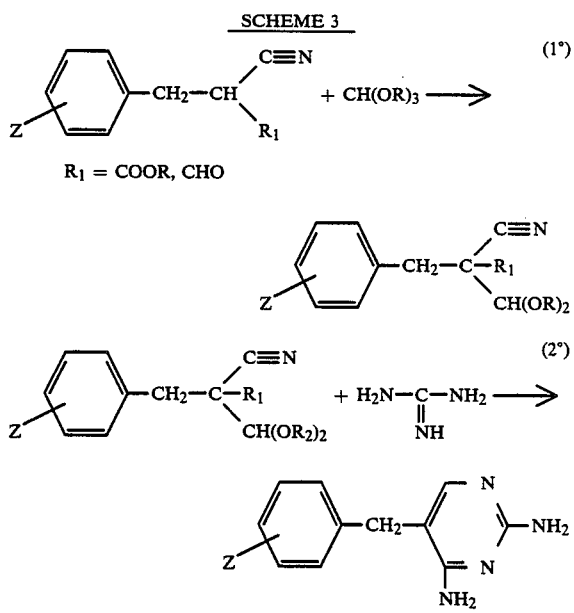

described in French Patent Document No. A-2354317.

No process has ever been described which uses as the starting material a 3-hydroxy-2-methylenephenylpropionitrile of the formula II:

II in which $R_1$, $R_2$, $R_3$ and $R_4$ have the same meanings as above.

According to the invention, the compounds of the formula II are reacted with an alkali metal alcoholate of the formula ROM, in which M is an alkali metal cation, in solution in a solvent, in the presence of an aliphatic ester, to give the compound of the formula III:

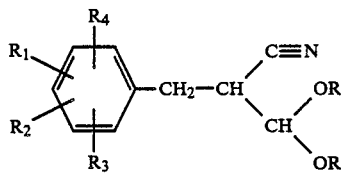

with which guanidine:

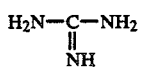

is reacted to give the compound of the formula I.

The alkali metal alcoholate can have from 1 to 4 carbon atoms; sodium methylate is preferred, in particular for reasons of cost and ease of handling, but it is also possible to use, for example, sodium ethylate or a mixture of sodium and potassium methylate.

It has also been found that alkali metal salts, such as potassium salts, accelerate particularly the rearrangement to the acetal III and the final condensation reaction with guanidine; they can be introduced into the medium in the form of a salt of a mineral or organic acid, such as a halide, formate, acetate or carbonate.

As the solvent, it is preferred to use a polar aprotic solvent, for example N-methylpyrrolidone or the like, hexamethylphosphotriamide or dimethyl sulfoxide. Preference is given to dimethyl sulfoxide, which in particular substantially accelerates the reaction and improves the yield; it can be used as a mixture with toluene, methanol or other inert solvents. The alcoholate can be introduced in the solvent, as a solid or dissolved in the corresponding alcohol.

The aliphatic ester is derived from a $C_1$ to $C_4$ alcohol and a carboxylic acid preferably not containing hydrogen on the carbon alpha to the carboxyl group, such as formic acid, pivalic acid or oxalic acid; formic acid is particularly preferred, as is methyl formate. It has in fact been found that esters, such as methyl acetate, only slightly improve the yield of the reactions leading to the formation of the compound III.

It is also possible to use alkyl esters of mineral acids which are inert towards the alcoholate used in the reaction, for example trimethyl phosphate or tetramethyl silicate.

Guanidine is generally marketed in the form of guanidine carbonate or hydrochloride; in view of its instability, it is preferably freed from its salt in situ; this can be done, when the reaction giving the compound III is complete, by introducing one equivalent of an alkali metal alcoholate, such as sodium methylate, into the reaction medium before the guanidine salt, or by introducing the necessary amount of alcoholate together with that required for the preparation of the acetal III.

In general, 1 to 2.5 mol of alkali metal alcoholate will be reacted with 1 mol of 3-hydroxy-2-methylenephenylpropionitrile in the presence of 1 to 2 mol of ester, preferably 2 to 2.5 mol of alcoholate. The amount of solvent used must be sufficient to enable the medium to be stirred; it must not be excessive, however, as the rate of the reactions drops off substantially with the concentration of the reactants.

If an alkali metal salt is introduced into the medium right at the beginning of the process, preference is given to the potassium salt of the acid corresponding to the ester used, introduced in an amount of about 0.1 to 0.5 mol per mol of nitrile.

The alkali metal alcoholate is added to the solution of the compound of the formula II at a temperature of between 0° C. and room temperature, i.e. 20°–25° C., and the reaction medium is then heated to between 60° and 80° C.; the reaction is slower if the temperature does not exceed 70° C., but the final product obtained is then easier to purify; the product III is condensed with guanidine at a temperature of between 80° C. and 120° C.

The conversion of the compound of the formula II to the compound of the formula III is thought to be accompanied by the formation of already known intermediates, such as the compound III described especially in French Pat. No. 1453056. In fact, if the reaction of sodium methylate with the compound of the formula II takes place at low temperature, it is possible to detect the compound of the formula IV:

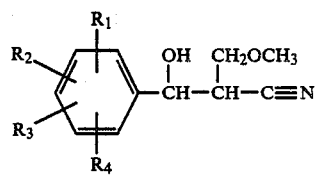

which dehydrates spontaneously in the absence of base to give the cinnamonitrile of the formula V:

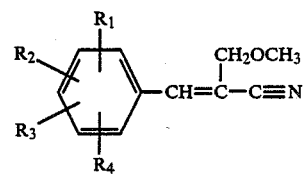

The product V is known; it has been shown not to react with guanidine to give the 2,4-diaminobenzylpyrimidine; its isomer V', on the other hand, reacts readily with guanidine; French Pat. No. 1266248 describes a reaction of this type, but the yield obtained in the example given is only 28%. It is therefore preferred to proceed via the compound III using a known type of reaction; in fact, reaction of sodium methylate with the compound V' leads, after isomerization, to the known compound III according to the equation:

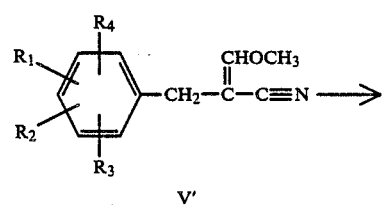

V'

-continued

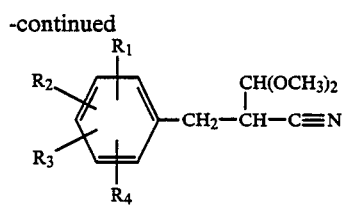

III

It has thus been found that when the compound III, isolated and purified, is reacted with guanidine in hot butanol solution, the crude pyrimidine of the formula I is obtained with a yield of 90 to 97%.

It has also been found, however, that when guanidine is reacted with the compound III without first isolating it from the reaction medium in which it has been prepared by the process of the invention, the pyrimidine is obtained in a yield of more than 80% relative to the starting compound of the formula II, this method being preferred. If, on the other hand, the reaction of the alkali metal alcoholate with the compound of the formula II is performed in the absence of an aliphatic ester, the final yield is less than 40%, and if guanidine and the compound of the formula II are reacted directly in butanol without proceeding via the compound III, the yield does not exceed 30%, demonstrating the great advantage of the process according to the invention.

The starting material II can be prepared by known methods, especially by reacting the aldehyde:

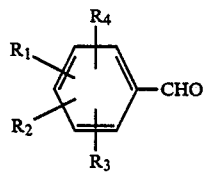

with acrylonitrile, $CH_2=CH-C\equiv N$, in the presence of an appropriately selected catalyst. It has been described in particular that the reaction of an aldehyde Z—CHO with acrylonitrile, catalyzed in British Pat. No. 1 168 000 by phosphines or in U.S. Pat. No. 3,743,669 by tricyclic tertiary amines such as quinuclidine, triethylenediamine or diazabicyclo-2,2,2-octane (hereafter called DABCO), makes it possible to obtain alpha-hydroxyacrylonitriles of the formula:

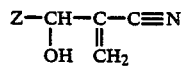

However, the examples mentioned in the above two references relate only to aliphatic aldehydes and the Applicant Company has found that the yields of the synthesis are appreciably lower for aromatic aldehydes, in particular under the operating conditions indicated in U.S. Pat. No. 2,743,669.

In fact, when trimethoxybenzaldehyde is dissolved in acrylonitrile and a catalytic amount of DABCO is added (0.1 mol per mol of aldehyde), the product of the formula II is obtained with a yield of only 50 to 60% after one week at room temperature, whereas if the reaction medium is heated, numerous by-products are formed without a substantial increase in the yield.

The invention therefore also relates to an improved process for the preparation of the compound of the formula II, by which process this compound is obtained from the aldehyde and acrylonitrile with a yield approaching the maximum and in all cases greater than 90%. This process involves a synthesis intermediate which has never been isolated and which is a complex consisting of two molecules of the compound of the formula II and one molecule of DABCO.

These crystalline complexes are stable; they can be recrystallized and the analyses which have been carried out (elemental analysis, IR and NMR spectra) have confirmed their structure. They are decomposed by reaction with an acid to give the DABCO salt and the compound of the formula II. These complexes are a further subject of the invention, as are also the compounds of the formula II prepared via the said complexes, and in particular:

the complex of the formula:

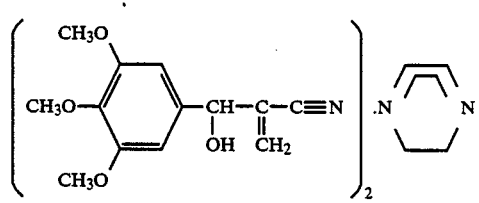

which melts at 111°-112° C. after recrystallization from toluene or isopropyl acetate;

the complex of the formula:

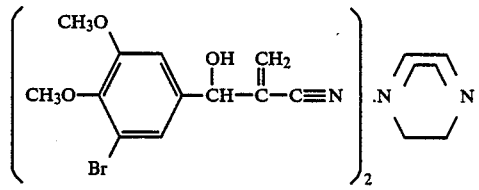

which melts at 94°-96° C.;

the complex of the formula:

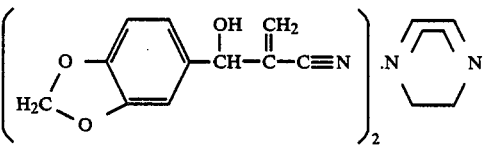

which melts at 89°-91° C.; or the complex of the formula:

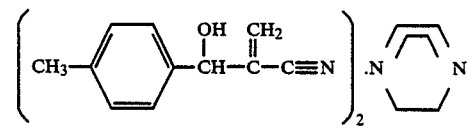

which melts at 94°-95° C.

These complexes are formed by reacting from 0.5 mol to 1 mol of DABCO with 1 mol of aldehyde in solution in acrylonitrile. It is preferred to use from 0.5 to 0.6 mol of DABCO. In certain cases, it is necessary to use a considerable excess of acrylonitrile in order to prevent the medium from solidifying. It is also possible to perform the reaction with only 1.2 to 1.5 equivalents of acrylonitrile in the presence of an appropriately selected third solvent in which the complex will precipitate. With solvents like toluene, cyclohexane, chloroform, methylene chloride, ethyl acetate, acetonitrile, dimethylformamide, methanol or ethanol, the reactions are very slow and the yields rather poor, more or less significant proportions of by-products being formed. On the other hand, tertiary butyl alcohol and solvents containing ether groups, such as dioxane, tetrahydrofuran, dimethoxymethane and ethers of ethylene glycol or diethylene glycol, give satisfactory results. These solvents can be used pure, mixed in variable proportions with one another or mixed with less than 20% of a protic solvent, thereby increasing the reaction rate. The protic solvent can be selected from the group comprising hydroxylated solvents and primary amides. Examples of hydroxylated solvents which may be mentioned in particular are pure or aqueous $C_1$-$C_4$ alcohols such as methanol, ethanol or 95% aqueous ethanol, and examples of primary amides which may be mentioned in particular are formamide or acetamide.

The reaction is preferably performed at room temperature, which avoids the formation of by-products.

When the reaction is complete, the complex formed can be isolated by filtration or decomposed immediately by adding an aqueous solution of acid to the medium, or it can be converted in situ to the cinnamonitrile of the formula V, from which the compound of the formula III is then prepared by a known process; if the medium contains a water-immiscible solvent, the two phases can be separated; the aqueous phase contains the salt of DABCO with the acid, from which the DABCO itself may be reprecipitated and recycled in a subsequent operation without special purification. The organic phase, which no longer contains DABCO, will be concentrated in vacuo to remove the solvent and unreacted acrylonitrile.

If the compound of the formula II is prepared by the process involving the formation of the DABCO complex, the pure diaminopyrimidine of the formula I is obtained with a yield of 80 to 85%, relative to the starting aldehyde, by appling the process according to the invention; the yield is substantially greater than the yields obtained by applying the processes described previously.

Examples of how to put the invention into effect are described below.

EXAMPLE 1

Preparation of 3-hydroxy-2-methylene-3-(3,4,5-trimethoxyphenyl)propionitrile

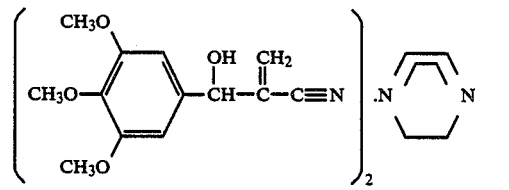

55 ml of acrylonitrile, 50 ml of dimethoxymethane, 20 g of formamide, 100 g of 3,4,5-trimethoxybenzaldehyde and 30 g of commercial-grade DABCO, or the equivalent amount of DABCO recovered at the end of a previous operation, are introduced into a 500 ml reactor fitted with a stirrer. A precipitate appears after a few hours and the reaction is complete after stirring for 20 to 36 hours.

The complex is then isolated by filtration of the reaction medium; a second crop is recovered after concentration of the filtrate; the yield is then greater than 90%.

The same complex is obtained by stirring 196 g of 3,4,5-trimethoxybenzaldehyde, 300 g of acrylonitrile and 60 g of DABCO at about 20° C. for 24 hours. The complex precipitates in the medium; a second crop is isolated by adding ethyl ether to the filtrate.

After recrystallization from three volumes of toluene, the complex melts at 111°-112° C. The NMR and IR spectra, which are consistent, show that the hydroxyls participate in hydrogen bonds.

(b) Freeing of the nitrile from its complex

The complex is dissolved in four volumes of 1,2-dichloroethane and the organic phase is washed with a 5N aqueous solution of hydrochloric acid until the pH of the aqueous phase is 4–4.5.

The two phases are then separated; the organic phase is washed with 100 ml of water and the solvent is then removed under reduced pressure. The thick residue solidifies; this is 3-hydroxy-2-methylene-3-(3,4,5-trimethoxyphenyl)propionitrile. After recrystallization from a toluene/heptane mixture (1/1), the product melts at 77°-79° C.

NMR spectrum (CDCl$_3$, TMS): 6.68 (s, 2H); 6.12 (dd, 2H); 5.25 (s, 1H); 3.85 (two s, 9H); 3.18 (1H exchangeable).

EXAMPLE 2

Preparation of 3-hydroxy-2-methylene-3-(3,4,5-trimethoxyphenyl)propionitrile without isolation of the complex The procedure of Example 1-a is followed except that, when the reaction is complete, 300 ml of 1,2-dichloroethane and 100 ml of 5N aqueous HCl are added instead of the reaction medium being filtered. The aqueous phase is then decanted and washed twice with 50 ml of 1,2-dichloroethane.

The organic phases are washed with water and combined and the solvent is evaporated off under reduced pressure. 127.5 g of 3-hydroxy-2-methylene-3-(3,4,5-trimethoxyphenyl)propionitrile are thus obtained starting from 100 g of aldehyde.

The aqueous solution of hydrochloric acid, containing the DABCO, is concentrated by evaporation under reduced pressure; when the water content is no more than 30%, the mixture is cooled and a sufficient amount of a solution of NaOH in methanol (c=10% w/v) is added in order to free the DABCO from its salt; after the sodium chloride has been filtered off, the methanol is removed under reduced pressure. The DABCO, which is recovered quantitatively by this method, can be re-used for a subsequent operation without additional purification.

EXAMPLE 3

Complex of 3-hydroxy-2-methylene-3-(3,4-methylenedioxyphenyl)-propionitrile with DABCO 15 g of 3,4-methylenedioxybenzaldehyde are stirred at room temperature with 5.6 g of DABCO and 20 ml of acrylonitrile for 48 hours; thin layer chromatography shows that no starting benzaldehyde remains. The reaction mixture is cooled to −10° C. and filtered to isolate the precipitate. This is washed with toluene and dried.

22 g of complex are thus isolated. A second crop of 3.5 g can be obtained after concentration of the mother liquors. The yield is about 95%. The complex can be recrystallized from toluene or isopropyl acetate. When pure, it melts at 89°–91° C. and is formed of 2 molecules of nitrile to one of DABCO.

EXAMPLE 4

Preparation of 2,4-diamino-5-(3,4,5-trimethoxybenzyl)pyrimidine 125.5 g of the nitrile prepared above are introduced into a 1 liter reactor together with 150 ml of toluene, 53 ml of methyl formate and 50 ml of dimethyl sulfoxide. The mixture is cooled to 0° C. and 210 ml of a 30% (w/v) solution of sodium methylate in methanol are added gradually, taking care to ensure that the temperature does not rise above 20° C.; the reaction medium is then heated slowly to 65°–70° C. and kept at this temperature for about 16 to 18 hours. It is then cooled to 30° C. and 120 ml of methanol are added, followed by 55 g of guanidine carbonate. The reaction medium is then heated again and the methanol and some toluene are distilled until the medium reaches an internal temperature of about 110° C. After one hour thirty minutes at this temperature, the cyclization is complete; the mixture is cooled to about 100° C. and the crude final product precipitates. The isolated precipitate is washed with water and then with acetone or dichloroethane to give 121.3 g of 2,4-diamino-5-(3,4,5-trimethoxybenzyl)-pyrimidine. After purification by the conventionl methods, 118 g of pure product are obtained, i.e. a yield of 79.8% relative to the starting trimethoxybenzaldehyde, when the nitrile has been prepared by the method described in Example 2.

EXAMPLE 5

Preparation of 2,4-diamino-5-(3,4,5-trimethoxybenzyl)pyrimidine 125.5 g of the nitrile are introduced into a one liter reactor together with 150 ml of toluene, 20 g of potassium formate, 53 ml of methyl formate and 50 ml of dimethyl sulfoxide; 230 ml of a 30% solution of sodium methylate in methanol are added, the temperature being kept below 20° C., and the reaction medium is then kept at about 65° C. for 10 to 12 hours. 64 g of guanidine carbonate are then added at about 30° C. The subsequent treatment of the reaction medium is as above. 125 g of crude final product are ultimately isolated, giving 121.4 g of pure product.

EXAMPLE 6

Preparation of 3-(3,4,5-trimethoxyphenyl)-2-methoxymethylacrylonitrile 55 ml of acrylonitrile, 50 ml of dimethoxymethane, 100 g of 3,4,5-trimethoxybenzaldehyde and 30 g of DABCO are introduced into a 500 ml reactor fitted with a stirrer. After stirring for 25 hours, 50 g of methyl formate and 100 ml of methanol are added and the mixture is stirred at room temperature for more than 24 hours until the 3-hydroxy-2-methylene-3-(3,4,5-trimethoxyphenyl)propionitrile has disappeared; the 3-(3,4,5-trimethoxyphenyl)-2-methoxymethylacrylonitrile formed is isolated or reacted with sodium methylate, after removal of the volatile reactants and solvents, to give the acetal of the formula III.

What is claimed is:

1. A process for the preparation of 2,4 diamino-5-benzylpyrimidines derivatives of formula I:

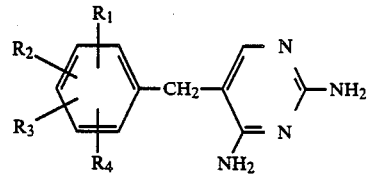

in which $R_1$, $R_2$, $R_3$, and $R_4$, which are identical or different, represent hydrogen, a $C_1$–$C_4$ alkyl group, a $C_1$–$C_4$ alkoxygroup, dialkylamino group in which the alkyl group is $C_1$–$C_3$ or a halogen atom, or $R_1$ and $R_2$ together represent a methylenedioxy group, which comprises: (a) reacting, in a liquid phase, at a temperature between about 0° C. and about 80° C., a 3-hydroxy-2-methylenephenylpropionitrile derivative of formula II:

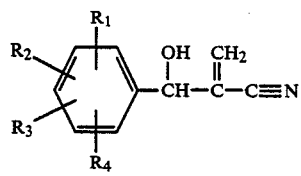

in which each of $R_1$, $R_2$, $R_3$ and $R_4$ is defined as above, with 1 to 2.5 molar equivalents of an alkali metal alcoholate of formulate ROM, in which M represents an alkali metal cation and R is a $C_1$–$C_4$ alkyl group, in the presence of an ester of an aliphatic alcohol to give the compound of formula III:

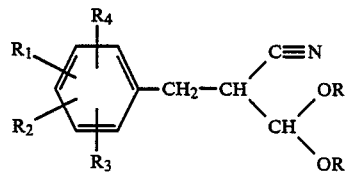

in which each of $R_1$, $R_2$, $R_3$, and $R_4$ is defined as above; and (b) reacting the compound of formula III with guanidine at a temperature between about 80° C. and about 120° C.

2. The process as claimed in claim 1, wherein at least one mol of ester is used per mol of propionitrile of the formula II.

3. The process as claimed in claim 1, wherein said liquid phase comprises a polar aprotic solvent.

4. The process as claimed in claim 1, wherein said liquid phase comprises a mixture of dimethyl sulfoxide and methanol.

5. The process as claimed in claim 1, wherein said liquid phase comprises a mixture of dimethyl sulfoxide, toluene and methanol.

6. The process as claimed in any one of claim 1, wherein the ester is derived from a $C_1$ to $C_4$ alcohol and a carboxylic acid selected from the group comprising formic acid, pivalic acid and oxalic acid.

7. The process as claimed in claim 6, wherein the ester is methyl formate.

8. The process as claimed in any one of claim 1, wherein an alkali metal salt of a carboxylic acid is introduced with the ester.

9. The process as claimed in any one of claim 1, wherein the guanidine is freed from one of its salts in situ by reaction with an alkali metal alcoholate.

10. The process as claimed in any one of claim 1, wherein the alcoholate is sodium methylate.

11. The process as claimed in any one of claim 1, wherein the compound of formula I is 2,4-diamino-5-(3,4,5-trimethoxybenzyl)pyrimidine.

12. The process as claimed in claim 1 wherein the compound of formula II is obtained by an addition reaction which comprises reacting, in a reaction medium, an aldehyde of the formula:

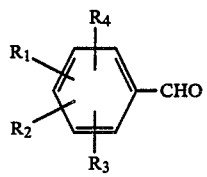

in which $R_1$, $R_2$, $R_3$ and $R_4$ are as defined as claim 1, with acrylonitrile, $CH_2=CH-C\equiv N$, in the presence of 0.5 to 1 equivalent, relative to the aldehyde, of diazabicyclo-2,2.2-octane.

13. The process as claimed in claim 12, wherein from 0.5 to 0.6 equivalent of diazabicyclo-2,2,2-octane is used.

14. The process as claimed in one of claim 12, wherein the addition reaction is performed in a solvent selected from the group comprising dioxane, tetrahydrofuran, dimethoxymethane, ethers of ethylene glycol and diethylene glycol, and tertiary butanol.

15. The process as claimed in any one of claim 14, wherein the solvent is dimethoxymethane.

16. The process as claimed in any one of claim 12, wherein the reaction medium also contains a protic solvent selected from the group comprising hydroxylated solvents and primary amides.

17. The process as claimed in claim 16, wherein said hydroxylated solvents comprise $C_1$ to $C_4$ alcohols.

18. The process as claimed in one of claim 1, wherein the compound of the formula III is obtained without isolating the nitrile of the formula II prepared by the process described in one of claim 12.

* * * * *